(12) United States Patent
Kim et al.

(10) Patent No.: US 9,101,261 B2
(45) Date of Patent: Aug. 11, 2015

(54) METHOD, MEDIUM, AND APPARATUS GENERATING HEALTH STATE BASED AVATARS

(75) Inventors: Youn-ho Kim, Hwaseong-si (KR); Woo-young Jang, Seoul (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 389 days.

(21) Appl. No.: 11/247,204

(22) Filed: Oct. 12, 2005

(65) Prior Publication Data

US 2006/0089543 A1    Apr. 27, 2006

(30) Foreign Application Priority Data

Oct. 12, 2004  (KR) .......................... 10-2004-0081351

(51) Int. Cl.
*A61B 5/00* (2006.01)
*G06F 3/00* (2006.01)
(Continued)

(52) U.S. Cl.
CPC .................. *A61B 5/00* (2013.01); *A61B 5/6887* (2013.01); *G06F 19/345* (2013.01);
(Continued)

(58) Field of Classification Search
CPC .................... A61B 5/7425–5/745; A61B 5/02; A61B 5/72; G06T 13/40; G06F 19/34–19/3493
USPC ......... 600/300–301, 306, 309, 310, 372, 379, 600/382–384, 386–393, 481, 508, 509, 529, 600/546, 547, 549; 128/920–925, 900–906; 715/700–713; 434/263–275
See application file for complete search history.

(56) References Cited

U.S. PATENT DOCUMENTS 6,032,119 A * 2/2000 Brown et al. ..................... 705/2
6,095,949 A    8/2000 Arai
(Continued)

FOREIGN PATENT DOCUMENTS

JP    07-204164    8/1995
JP    9-231413     9/1997
(Continued)

OTHER PUBLICATIONS

Bianchi, N. et al, "Modeling Multimodal Expression of User's Affective Subjective Experience", User Modeling and User-Adapted Adapted Interaction 12: 49-84, 2002.*

(Continued)

*Primary Examiner* — William Thomson
*Assistant Examiner* — Marie Archer
(74) *Attorney, Agent, or Firm* — Harness, Dickey & Pierce, P.L.C.

(57) ABSTRACT

A method, medium, and apparatus extracting avatar parameters using an avatar transformation algorithm from health state information measured from a user and generating an avatar using the extracted parameters. In the apparatus, a state analysis unit receives at least one among a bio-signal and questionary information of a user and outputs health state information, a parameter extraction unit extracts parameters defining an avatar image, and an avatar generation unit generates the avatar image using the parameters. By providing the method, medium, and apparatus, it is possible to provide a user with a convenience in recognizing his health state by generating an avatar image describing the user's future health state as well as the user's current health state. Further, it is possible to induce a user to manage his health constantly by maintaining a user's with the avatar image change.

58 Claims, 10 Drawing Sheets

(51) Int. Cl.
  *G06T 13/40* (2011.01)
  *G06F 19/00* (2011.01)
  *G06T 13/00* (2011.01)
  *A61B 5/0402* (2006.01)
  *A61B 5/053* (2006.01)

(52) U.S. Cl.
  CPC ....... *G06F 19/3406* (2013.01); *G06F 19/3431* (2013.01); *G06F 19/3437* (2013.01); *G06T 13/40* (2013.01); *A61B 5/0402* (2013.01); *A61B 5/0537* (2013.01); *A61B 5/441* (2013.01)

(56) References Cited

U.S. PATENT DOCUMENTS

| | | | | |
|---|---|---|---|---|
| 6,110,109 | A | * | 8/2000 | Hu et al. .................. 600/300 |
| 6,692,258 | B1 | * | 2/2004 | Kurzweil et al. ............ 434/262 |
| 6,817,979 | B2 | * | 11/2004 | Nihtila ..................... 600/300 |
| 6,820,112 | B1 | * | 11/2004 | Matsuda et al. ............. 709/203 |
| 2002/0055855 | A1 | | 5/2002 | Cule et al. |
| 2003/0065255 | A1 | * | 4/2003 | Giacchetti et al. .......... 600/407 |
| 2004/0002634 | A1 | | 1/2004 | Nihtila |
| 2005/0101845 | A1 | * | 5/2005 | Nihtila ..................... 600/300 |

FOREIGN PATENT DOCUMENTS

| | | |
|---|---|---|
| JP | 11-4820 | 1/1999 |
| JP | 2000-271091 | 10/2000 |
| JP | 2001-275991 | 10/2001 |
| JP | 2002-095637 | 4/2002 |
| JP | 2002-190034 | 7/2002 |
| JP | 2002-233507 | 8/2002 |
| JP | 2002-291704 | 10/2002 |
| JP | 2003-235834 | 8/2003 |
| JP | 2004-8659 | 1/2004 |
| JP | 2004-121530 | 4/2004 |
| JP | 2004-130142 | 4/2004 |
| JP | 2004-185437 | 7/2004 |
| JP | 2006-262010 | 9/2006 |
| KR | 10-2001-0055569 | 7/2001 |
| KR | 10-2002-0008934 A | 1/2002 |
| KR | 10-2002-0050251 | 6/2002 |
| WO | 2004/056266 | 7/2004 |
| WO | 2004/059551 | 7/2004 |

OTHER PUBLICATIONS

Bos, J, et al. Believable Information Delivery for Prototype I Avatar Arena, Report prepared for the project known as "Embodied Believable Agents", Date of preparation: Oct. 29, 200, p. 1-40.*
Lisetti, C. et al. "Developing multimodal intelligent affective interfaces for tele-home health care", Int. J. Human-Computer Studies 59 (2003) 245-255.*
Lyons, M, et al. "Avatar Creation using Automatic Face Recognition", Proceedings, ACM Multimedia 98, Bristol, England, Sep. 1998, pp. 427-434.*
Nasoz, F, et al. "Emotion recognition from physiological signals using wireless sensors for presence technologies", Cogn Tech Work (2004) 6: 4-14.*
Stava, R. M in "Medical Applications of virtual reality", Virtual Reality handbook, Chapter 55, 1999, p. 1-24.*
Tomio Watanabe; "Embodied Communication Technology for Advanced Media Society", Correspondences on Human Interface, vol. 5, No. 1, pp. 55-60, Human Interface Society, Jan. 24, 2003.
Kensaku Honda, "Change in Expression of Avatar Using Information about Brain Waves", Information Processing Society of Japan, Mar. 12, 2002, pp. 4-575-4-578.
Japanese Office Action issued Jan. 18, 2011, corresponds to Japanese Patent Application No. 2008-081795.
Japanese Office Action issued Jan. 11, 2011, corresponds to Japanese Patent Application No. 2005-285360.
Japanese Office Action issued Nov. 22, 2011 corresponds to Japanese Patent Application No. 211-20292.
Japanese Decision of Rejection issued Jun. 21, 2011, corresponds to Japanese Patent Application No. 2005-285360.
Japanese Notice of Preliminary Reexamination issued Jan. 4, 2012 corresponds to Japanese Patent Application No. 2011-22771.
Suphattharachai Chomphan, "Multi-Pulse Based Code Excited Linear Predictive Speech Coder with Fine Granularity Scalability for Tonal Language", Journal of Computer Science 6 (11), pp. 1267-1271, ISSN1549-3636, 2010 Science Publications.
Japanese Notice of Rejection mailed May 17, 2011 corresponds to Japanese Patent Application No. 2008-081795.
Korean Intellectual Property Office Notice to Submit Response Issued Apr. 14, 2006.

* cited by examiner

FIG. 8
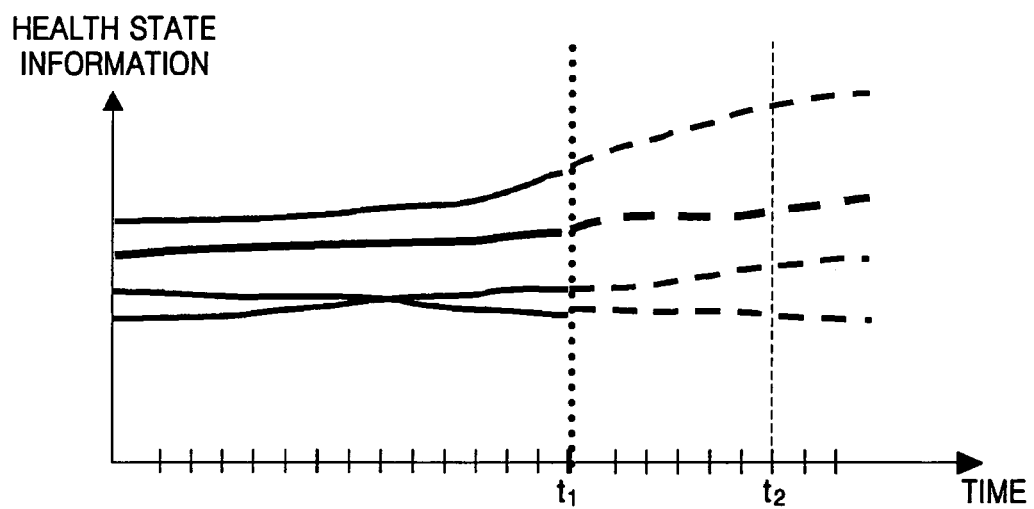
FIG. 9A  FIG. 9B
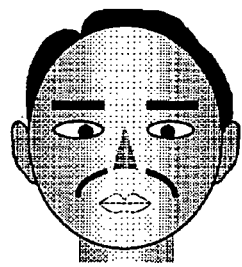 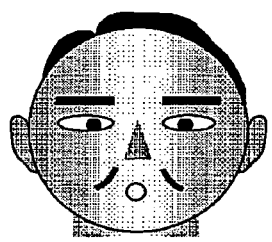

METHOD, MEDIUM, AND APPARATUS GENERATING HEALTH STATE BASED AVATARS

CROSS-REFERENCE TO RELATED APPLICATIONS

This application claims the priority of Korean Patent Application No. 10-2004-0081351, filed on Oct. 12, 2004, in the Korean Intellectual Property Office, the disclosure of which is incorporated herein in its entirety by reference.

BACKGROUND OF THE INVENTION

1. Field of the Invention

Embodiments of the present invention relate to a method, medium, and apparatus generating an avatar, and more particularly, to a method, medium, and apparatus extracting avatar parameters, using an avatar transformation algorithm, from health state information measured from a user and generating an avatar using the extracted parameters.

2. Description of the Related Art

Generally, results obtained by measuring a patients electrocardiogram signal, ultrasonic signal, body fat rate, and/or body mass index (BMI) have been used to monitor a patient's current health state or estimate future health states. However, since the measurement results are typically only described in terms of technical numerical values or graphs, it is difficult for the general public, who may have no medical knowledge, to understand their current health state, estimate future health states from the measurement results, or use the results in managing their health or disease prevention.

Therefore, recently, methods have been introduced for generating and displaying a user's health state in form of an image using health information measured from a user so that a user may easily check his health state with his natural eye. For the methods of generating a user's health state in form of an image, there exists a method of generating an avatar image based on an obesity degree, using an exercise amount and an ingested calorie amount, as input by a user.

An avatar, an animation character which may behave on behalf of a user in cyber space, for example, is a virtual body representing a user is mainly graphically constructed. The related art avatars are mostly two-dimensional images, but recently three-dimensional (3D) characters have been used, taking advantages of a cubic effect and a reality sense thanks to developments in computer graphic technology. For example, such 3D avatars have been widely used in cyber shopping malls, virtual education, and virtual offices, as well as in a chatting or in on-line gaming.

In the case of monitoring a user's health state, using the related art method as described above, it is difficult for a user who has no medical knowledge to check his health state. Even when using an avatar, a user can only check his level of obesity using only several predetermined avatar images, i.e., there is nothing individually generated for the user.

SUMMARY OF THE INVENTION

Embodiments of the present invention set forth a method, medium, and apparatus extracting parameters making up an avatar using an avatar transforming algorithm from health state information measured from a user, and generating an avatar modified in various ways based on the extracted parameters to overcome the aforementioned conventional drawbacks in checking a user's health state.

To achieve the above and/or other aspects and advantages, embodiments of the present invention include an apparatus for generating an avatar image using parameters, the apparatus including a state analysis unit to receive at least one of a bio-signal and questionary information of a user to analyze a user's health state, and to output health state information of the user, a parameter extraction unit to receive the health state information, and to extract parameters defining the avatar image by implementing a formula relating the health state information with the parameters, and an avatar generation unit to generate the avatar image using the parameters.

The state analysis unit may receive the at least one of the bio-signal and questionary information of the user and estimates the health state of the user for a predetermined period of time to output future health state information for the user.

In addition, the state analysis unit may include a bio-signal analysis unit to receive at least the one of the bio-signal and questionary information of the user and analyzing the user's health state to output the health state information, a storage medium to store the health state information, a controller to obtain the health state information from the bio-signal analysis unit to be stored in the storage medium, a regression formula obtaining unit to obtain a regression formula representing a temporal change in the health state information, using the health state information of the user stored in the storage medium, and a health state estimation unit to receive the health state information of the user from the bio-signal analysis unit and to output a user's future health state information, using the regression formula and the health state information.

The bio-signal may include at least one of an electrocardiogram signal, an ultrasonic signal, EDA (electrodermal activity), a body temperature, and a body fat rate. Further, the questionary information may include at least one of information of a habit, a syndrome, a stature, a weight, and a waist measure of the user.

The health state information may include information of at least one of whether a hospital visit is required, a stress/fatigue degree, a health age, a skin state, an obesity degree, a body portion balance degree, a heart health degree, a digestive organ health degree, and a respiratory organ health degree. Here, the body portion balance degree may be representative of being derived using an eight-point tactile electrodes method.

The parameters may include at least one of a facial muscle variation rate, a facial skin color variation rate, a facial wrinkle variation rate, a facial width variation rate, a heart size variation rate, a heart color variation rate, a color variation rate of an abnormal portion in a digestive organ, a color variation rate of an abnormal portion in a respiratory organ, and a size variation rate for each body portion depending on a body balance.

The apparatus may further include a display unit to display the generated avatar image.

In addition, the apparatus may further include a transmission unit to transmit data of the generated avatar image to an remote station or remote apparatus.

To achieve the above and/or other aspects and advantages, embodiments of the present invention include a method for generating an avatar image using parameters, including analyzing a user's health state using at least one of a bio-signal and questionary information of the user, receiving information of the analyzed health state to obtain a formula relating health state information of the user and parameters, extracting the parameters, and generating the avatar image using the extracted parameters.

The analyzing may include estimating the user's health state for after a predetermined period of time using the at least one of the user's bio-signal and the questionary information.

In addition, the analyzing may include analyzing the user's health state using the at least one of the bio-signal and the questionary information of the user, obtaining a regression formula representing a temporal change in the health state information from the analyzed user's health state, using the health state information, and generating future health state information of the user of after a predetermined period of time, using the health state information and the regression formula.

To achieve the above and/or other aspects and advantages, embodiments of the present invention include a medium including computer readable code to implement embodiments of the present invention.

To achieve the above and/or other aspects and advantages, embodiments of the present invention include an apparatus for generating an avatar image using parameters, the apparatus including a state analysis means for outputting health state information of a user, a parameter extraction means for extracting parameters defining the avatar image by implementing a formula relating the health state information with the parameters, and an avatar generation means for generating the avatar image using the extracted parameters.

The method for generating the avatar may further include: displaying the generated avatar; and transmitting the generated avatar image data to the outside.

The method for generating the avatar can be written as computer programs and can be implemented in general-use digital computers that execute the programs using a computer-readable recording medium.

Additional aspects and/or advantages of the invention will be set forth in part in the description which follows and, in part, will be apparent from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 8 graphically explains a method for obtaining a regression formula for estimating a future health state based on a current health state, according to an embodiment of the present invention;

FIGS. 9A-9B illustrate avatars estimating a future health state based on a present health state;

DETAILED DESCRIPTION OF THE PREFERRED EMBODIMENTS

Figure 1:
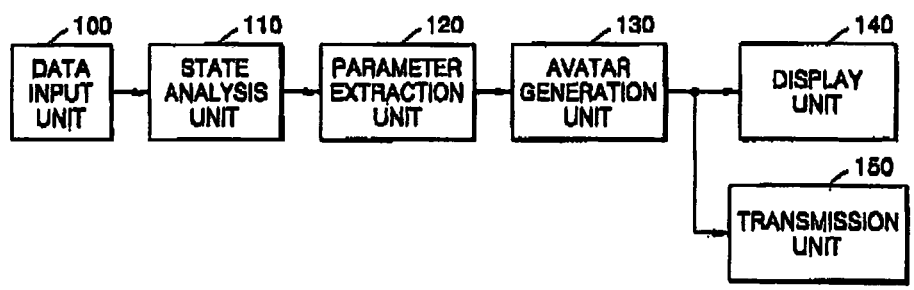
FIG. 1 illustrates an apparatus for generating an avatar, according to an embodiment of the present invention.

Reference will now be made in detail to embodiments of the present invention, examples of which are illustrated in the accompanying drawings, wherein like reference numerals refer to the like elements throughout. Embodiments are described below to explain the present invention by referring to the figures.

FIG. 1 illustrates an apparatus for generating an avatar, according to an embodiment of the present invention. The apparatus for generating the avatar can include a data input unit 100, a state analysis unit 110, a parameter extraction unit 120, an avatar generation unit 130, a display unit 140, and a transmission unit 150. Similar to FIG. 1, a method for generating the avatar will also be described concurrently below, referencing operations in FIG. 10, in connection with this apparatus.

Figure 10:
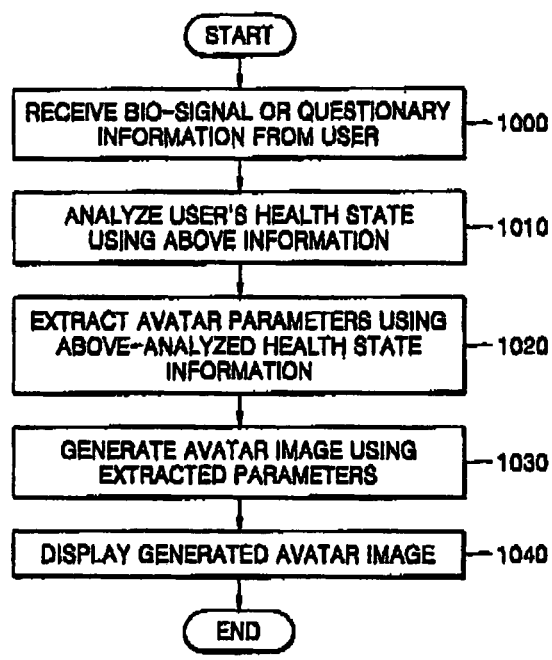
FIG. 10 illustrates a flowchart for a method to generate an avatar, according to an embodiment of the present invention.

The data input unit 100 can receive a bio-signal having information such as an electrocardiogram signal, an ultrasonic signal, electrodermal activity (EDA), a body temperature, and/or a body fat rate, which may have been measured from a user, and/or questionary information in which a user may have provided answers to questions related to the health state of the user, e.g., as in operation 1000 of FIG. 10. It may be desirable for the apparatus generating the avatar to use results obtained by measuring an electrocardiogram signal or a body fat rate directly from a user, as well as data from an electrocardiogram measuring device or a body fat rate measuring device.

The state analysis unit 110 can receive a bio-signal or questionary information from the data input unit 100 to analyze a user's health state using the received information, e.g., as in operation 1010 of FIG. 10. The state analysis unit 110 can analyze a current health state based on a user's bio-signal or received questionary information, and estimate a desired future health state, using a regression formula obtained based on past health data and the analyzed current health state, thereby possibly outputting a user's future health state information.

It may also be desirable for the state analysis unit 110 to analyze health states such as a first screening judgment degree (Hs), a stress/fatigue degree (St), a health age (Ha), a skin state (Ag), and/or an obesity degree (Ob) of a user, and also output the health state degrees in terms of numerical values.

The first screening judgment degree (Hs), which may be a numerical value representing a health state regarding whether a hospital visit is necessary for a user, may be computed from basic inquiries generally used in a hospital, e.g., questionary results related to living habits or disease syndromes.

The stress/fatigue degree (St) can be computed using a standard deviation for differences of intervals of adjacent rate ratio (RR) waves in an electrocardiogram and a ratio of a low frequency (LF) and a high frequency (HF) obtained through a heart rate variability (HRV) spectrum analysis of an electrocardiogram, for example. The LF, which reflects activation of a sympathetic system, is a power value for a low frequency region (0.04-0.15 Hz) in the HRV spectrum of the electrocardiogram and the HF, which reflects activation of a sympathetic system, is a power value for a high frequency region (0.15-0.4 Hz) in the HRV spectrum of the electrocardiogram.

The health age (Ha) can be computed from user questionary results for measuring a health age, used in a National Health Insurance Corporation or a hospital, for example. The skin state (Ag) can be computed from an ultrasonic signal or an EDA and the obesity (Ob) can be computed from a BMI, which is a value obtained by dividing a current weight by a square of a stature, a waist measure, and a body fat rate measured by a body fat measuring device, for example.

The parameter extraction unit 120 receives information regarding a user's health state from the state analysis unit 110 and extracts avatar parameters using an avatar transformation algorithm, i.e., a relation formula between the health state information set in advance and the avatar parameters, e.g., as in operation 1020 of FIG. 10. The avatar parameters and the avatar transformation algorithm will be described in more detail with following reference to FIGS. 2 and 4.

The avatar generation unit 130 can receive parameters defining an avatar from the parameter extraction unit 120 and generates avatar data using the parameters, e.g., as in operation 1030 of FIG. 10. The display unit 140 can then display the avatar representing a user's health state using the generated avatar data, e.g., as in operation 1040 of FIG. 10.

It may be desirable for the apparatus to generate the avatar to further include the transmission unit 150 for transmitting/distributing the generated avatar data, generated by the avatar generation unit 130. For example, the transmission unit 150 can transmit the generated avatar data representing a user's health state so that the user's health state may be checked at a remote station or apparatus.

Figure 2:
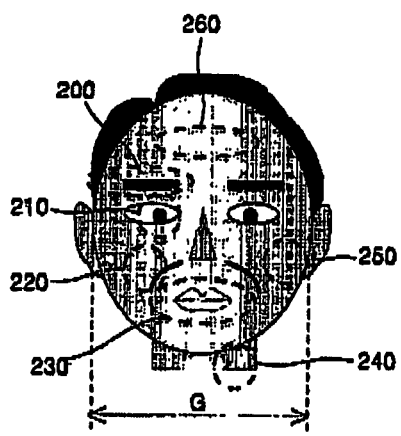
FIG. 2 illustrates facial regions, modified by parameters, making up an avatar, according to an embodiment of the present invention.

FIG. 2 illustrates facial regions, modified by parameters, making up an avatar, according to an embodiment of the present invention, with the facial regions expressing a user's health state in terms of a facial muscular change, a skin color change, a facial wrinkle change, and a facial width change, for example.

In a face avatar, the regions that change based on the health state are modifiable by each parameter, such that the images of the regions set by each parameter change depending on values of the parameters.

The parameter extraction unit 120 can receive user's health state information, such as a first screening judgment degree (Hs), a stress/fatigue degree (St), a health age (Ha), a skin state (Ag), and/or an obesity degree (Ob) of a user from the state analysis unit 110, and can perform computation using the following equation 1, to extract the avatar parameters.

In the following Equation 1, A is a parameter representing a facial muscular change rate for a region 200 of FIG. 2, B is a parameter representing a facial muscular change rate for a region 210, C is a parameter representing a facial muscular change rate for a region 220, D is a parameter representing a facial muscular change rate for a region 230, E is a parameter representing a facial skin color change rate for regions 240 and 250, F is a parameter representing a facial wrinkle change rate for a region 260, and G is a parameter representing a facial width change rate, for example. The image generated by each parameter can also be symmetric with respect to right and left.

$$A = a1 \times Hs + a2 \times St + a3 \times Ha + a4 \quad \text{Equation 1}$$

-continued $$B = b1 \times St + b2 \times Hs + b3 \times Ha + b4$$

$$C = c1 \times St + c2 \times Hs + c3 \times Ha + c4 \times Ag + c5$$

$$D = d1 \times St + d2 \times Hs + d3 \times Ha + d4$$

$$E = e1 \times St + e2 \times Hs + e3 \times Ag + e4$$

$$F = f1 \times Ha + f2 \times Ag + f3$$

$$G = g1 \times Ob + g2$$

In Equation 1, a1, a2, a3, a4, b1, b2, b3, b4, c1, c2, c3, c4, c5, d1, d2, d3, d4, e1, e2, e3, e4, f1, f2, f3, g1, g2 may be parameter constants.

Figure 3A:
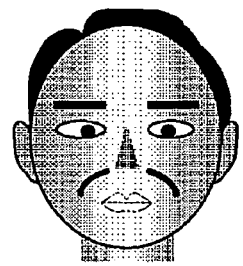
FIGS. 3A-3D illustrate avatars generated using different parameters, e.g., modifying the regions of FIG. 2, according to an embodiment of the present invention.
Figure 3B:
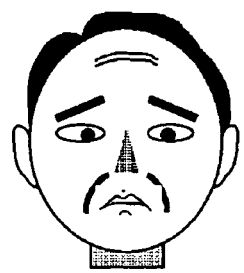
Figure 3C:
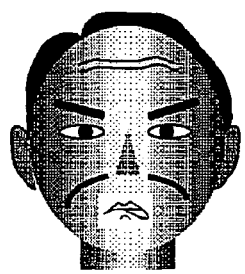
Figure 3D:
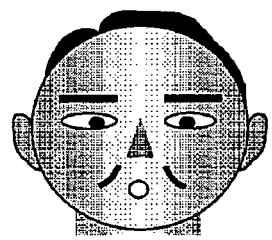

FIGS. 3A-3D illustrate avatars generated using the avatar parameters of FIG. 2, for example, with FIG. 3A illustrating an avatar generated representing a user's health state being normal, FIG. 3B illustrating an avatar representing a user's weak health state, FIG. 3C illustrating an avatar representing a user being under a lot of stress, and FIG. 3D illustrating an avatar representing a user being in an obese state.

Figure 4:
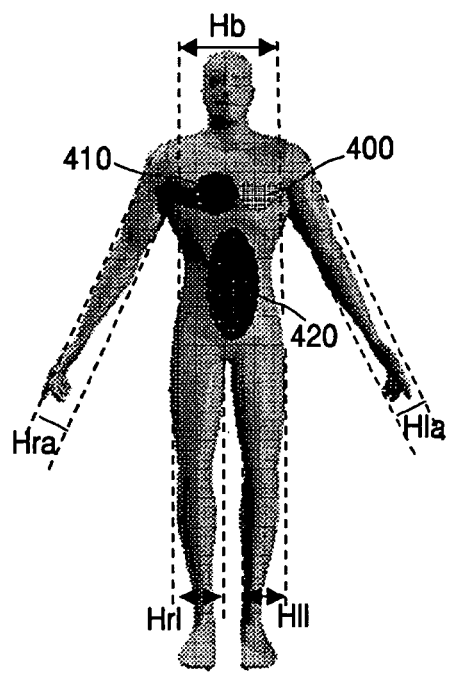
FIG. 4 illustrates regions of an avatar modifiable by parameters, according to an embodiment of the present invention.

FIG. 4 illustrates regions of an avatar modifiable by parameters, according to an embodiment of the present invention expressing a user's health state focusing on a particular body portion balance degree, a heart health degree, a digestive organ health degree, and a respiratory organ health degree, for example.

The body portion balance degree may be based on parameters of Hb, Hra, Hla, Hll, Hrl, and may desirably include parameters computed using a body fat rate measuring method for each portion, e.g., using an eight-point tactile electrode method.

Here, Hb may be a parameter representing a body fat rate of the trunk, Hra may be a parameter representing a body fat rate of the right arm, Hla may be a parameter representing a body fat rate of the left arm, and Hll may be a parameter representing a body fat rate of the left leg, and Hrl may be a parameter representing a body fat rate of the right leg.

The parameter extraction unit 120 may receive, for example, from the state analysis unit 110, a user's health state information such as a standard deviation of differences between intervals of adjacent RR waves in an electrocardiogram (SDSD), a root mean square (RMS) of differences between intervals of adjacent RR waves in the electrocardiogram (RMSSD), a rate in which an interval of adjacent RR waves in the electrocardiogram is more than 50 ms (pNN50), whether a user is under an arrhythmia state (AM), digestive organ-related questionary results (JS), respiratory organ-related questionary results (RS), and can perform computations using the following Equation 2, for example, to extract a heart health degree, a digestive organ health degree, and/or a respiratory organ health degree.

$$I = i1 \times SDSD + i2 \times RMSSD + i3 \times pNN50 + i4 \times AM + i5 \quad \text{Equation 2}$$

$$J = j1 \times JS + j2$$

$$K = k1 \times RS + k2$$

Here, in Equation 2, i1, i2, i3, i4, i5, j1, j2, k1, k2 may be parameter constants.

I is a parameter representing a heart health degree for a region 400 in FIG. 4. It may be desirable for the region 400 of the avatar, based on the parameter 1, to represent a red color image, of a standard size, when the heart health degree is normal, represent a red color image, of a small size, when the heart health degree is abnormal, and represent a gray color image when the heart is in arrhythmia.

J is a parameter representing a respiratory organ health degree for a region 410 in FIG. 4, and may be desirable for the region 410 of the avatar, based on the parameter J, to represent a skin color image when the respiratory organ health degree is normal and represent a gray color image when the respiratory organ health degree is abnormal.

K is a parameter representing a digestive organ health degree for a region 420 in FIG. 4, and it may be desirable for the region 420 of the avatar, based on the parameter K, to represent a skin color image when the digestive organ health degree is normal and represent a gray color image when the digestive organ health degree is abnormal.

Figure 5:
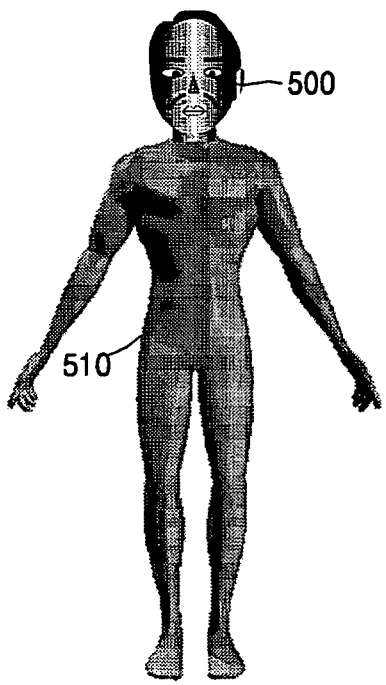
FIG. 5 illustrates an avatar generated using parameters, e.g., parameters modifying the regions illustrated in FIGS. 2 and 4, according to an embodiment of the present invention.

FIG. 5 illustrates a avatar generated using parameters, e.g., parameters modifying the regions illustrated in FIGS. 2 and 4, according to an embodiment of the present invention. By combining a face avatar, generated using the parameter modified regions of FIG. 2, for example, with the trunk, avatar, generated using the parameter modified regions of FIG. 4, for further example, it is possible to generate a whole avatar image illustrating the whole health state of a user.

Figure 6:
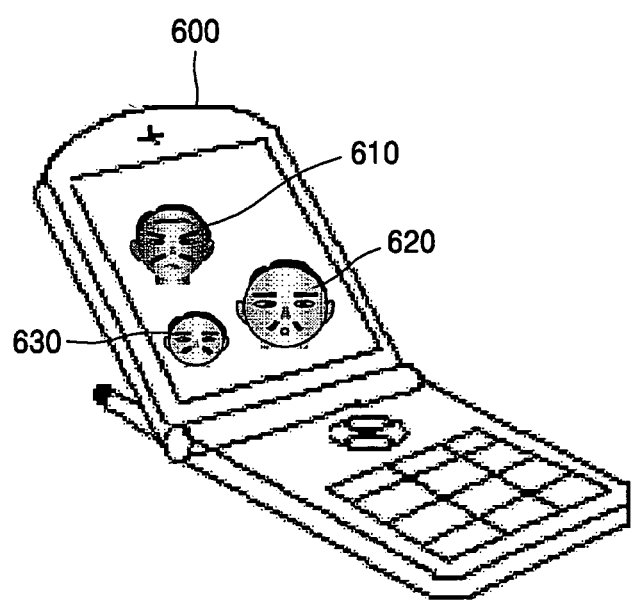
FIG. 6 illustrates an apparatus for receiving and displaying data of an avatar, generated based on a health state of a user, according to an embodiment of the present invention.

FIG. 6 illustrates an apparatus for receiving and displaying data of the generated avatar. Referring to FIG. 6, it may be desirable to display avatar image data, generated by the above-described operations, using a cellular phone 600, a personal digital assistant (PDA) (not shown), or a television (TV), for example. Further, the transmission unit 150 of FIG. 1 may transmit the generated avatar image data to the remote cellular phone 600, e.g., so that a user can see health state representing avatars 610, 620, and 630 of people desired by the user using the cellular phone 600, such that the health state of those people can be checked.

Figure 7:
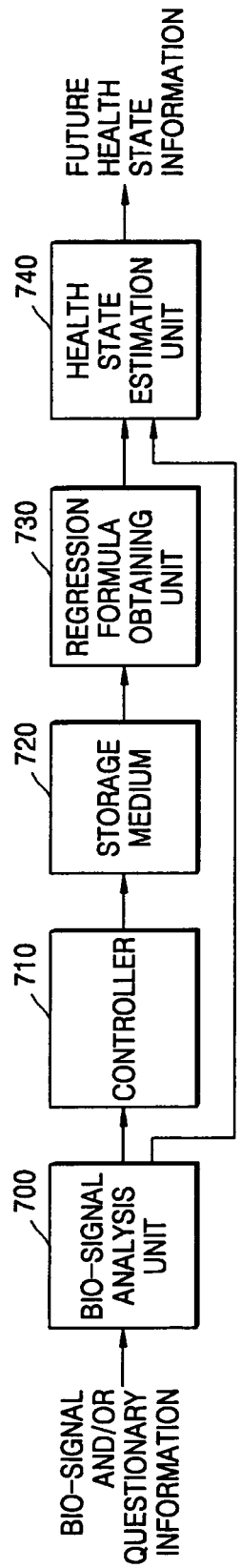
FIG. 7 illustrates a state analysis unit, e.g., the state analysis unit of FIG. 1, according to an embodiment of the present invention.

FIG. 7 illustrates an embodiment of a state analysis unit, e.g., the state analysis unit of FIG. 1. The illustrated state analysis unit may include a bio-signal analysis unit 700, a controller 710, a storage medium 720, a regression formula obtaining unit 730, and a health state estimation unit 740, for example. Similar to FIG. 7, a method for estimating a user's future health state using a user's current bio-signal or questionary information will also be described concurrently below, referencing operations in FIG. 11, in connection with this state analysis unit.

Figure 11:
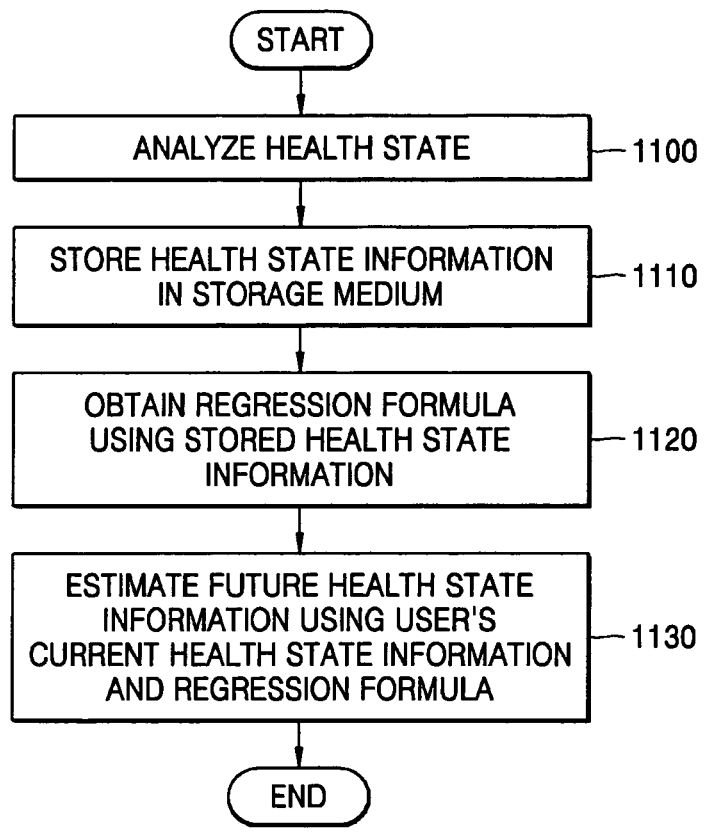
FIG. 11 illustrates a flowchart for a method to estimate a future health state based on a current health state, according to an embodiment of the present invention.

The bio-signal analysis unit 700 can receive bio-signals such as an electrocardiogram signal, an ultrasonic signal, a body fat rate, a waist measure, and/or a body mass index (BMI) measured from a user for a predetermined period of time, and/or questionary information, and analyzes a user's health state for each time band, e.g., as in operation 1100 of FIG. 11. The controller 710 can receive a user's health state information from the bio-signal analysis unit 700 to store the health state information in the storage medium 720, for each time band, e.g., as in operation 1110 of FIG. 11.

The regression formula obtaining unit 730 can obtain a regression formula describing a user's health state information change depending on time, using the health state information for each time band stored in the storage medium 720, e.g., as in operation 1120 of FIG. 11.

The health state estimation unit 740 may receive from a user a date on which a user desires to see his future health state, and may input the date into the regression formula to estimate and output user's desired future health state information, e.g., as in operation 1130 of FIG. 11.

FIG. 8 graphically explains a method for obtaining a regression formula for estimating a future health state based on a current health state, according to an embodiment of the present invention. With the illustrated graph, it is possible to analyze a health state information change based on the progression of time, obtain the regression formula using health state information of up to the current time $t_1$, and estimate health state information for a time point $t_2$ by inputting the time $t_2$, for which a health state will be estimated, into the computed regression formula.

It may be desirable that the state analysis unit receives, from a user, the point in time in which a user desires to know his/her health state, e.g., a time point after one month, six months, or one year to estimate health state information at a time point desired by a user, using the regression formula.

FIGS. 9A-9B illustrate avatars estimating a future health state based on a present health state, where FIG. 9A illustrates an avatar representing a current health state and FIG. 9B illustrates an avatar generated by estimating a future health state. As an example, a user may be able to estimate that his current health state is in a state of high probability of becoming obese, by checking an avatar change illustrated in FIG. 9B from the current state in FIG. 9A.

Figure 12A:
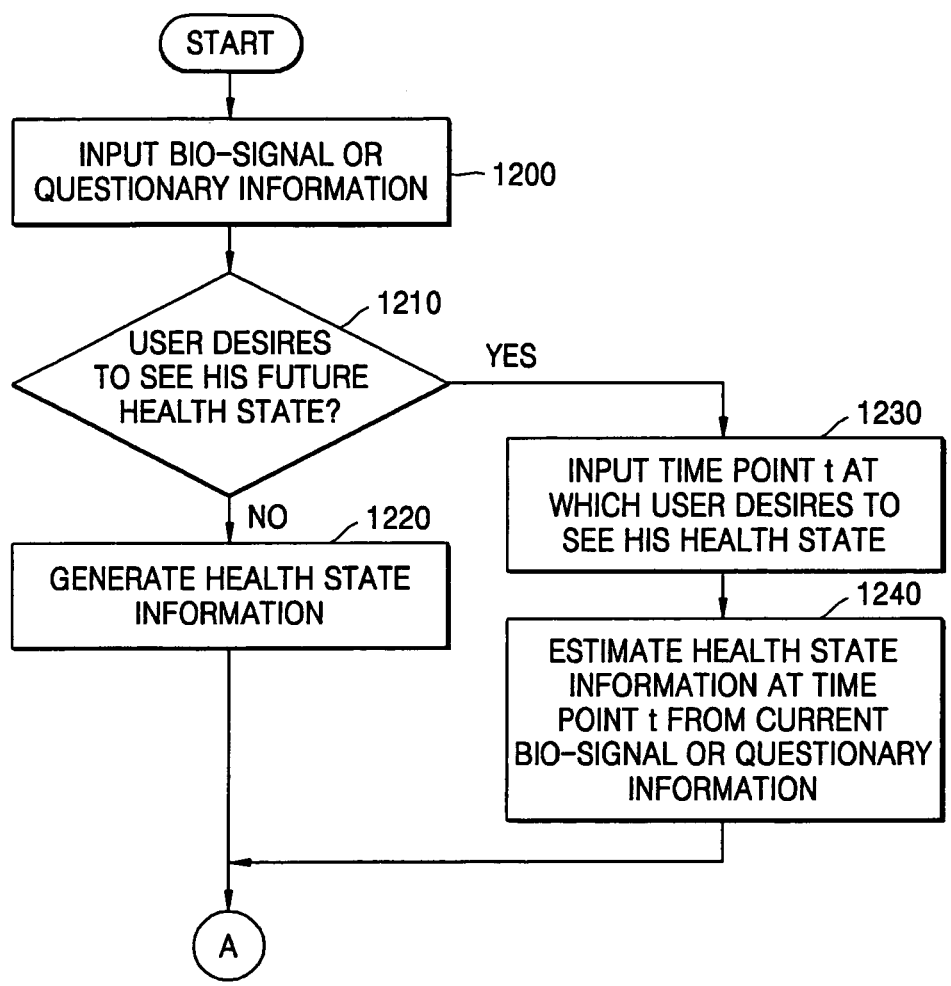
FIG. 12A-12B illustrate a flowchart for a method to generate an avatar, according to an embodiment of the present invention.
Figure 12B:
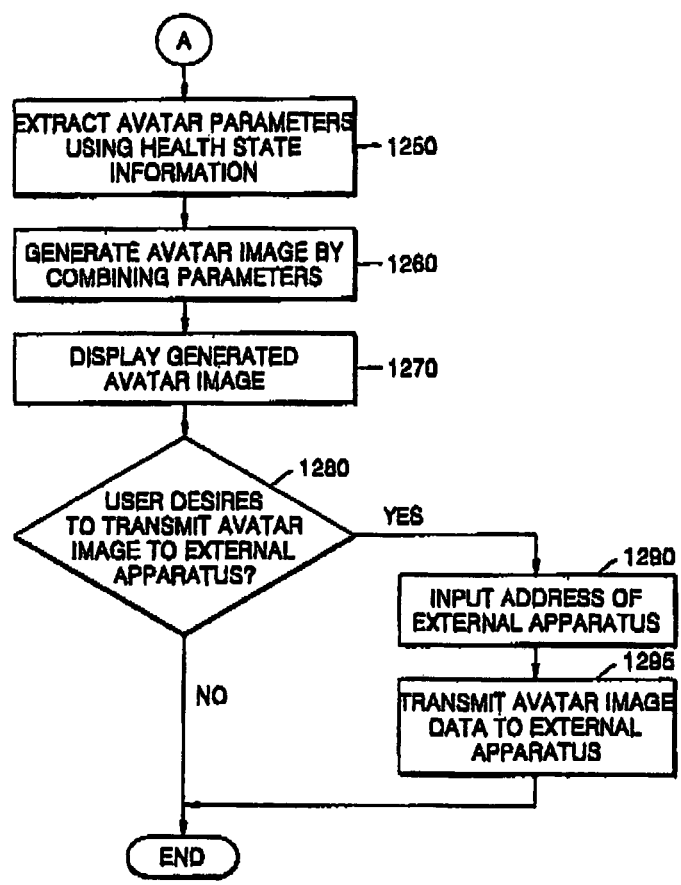

FIGS. 12A-12B illustrate a flowchart for a method to generate an avatar, according to an embodiment of the present invention. A data input unit, such as the data input unit 100 of FIG. 1, can receive a bio-signal having information such as an electrocardiogram signal, an ultrasonic signal, a body fat rate, a waist measure, and/or a body mass index which have been measured from a user, and/or questionary information in which a user has given answers to questions related to a predetermined health state, in operation 1200.

A state analysis unit, such as the state analysis unit 110 of FIG. 1, can determine whether a user desires to check a future health state, operation 1210. If a user desires to determine a current health state, the state analysis unit may generate current health state information using the bio-signal or questionary information, in operation 1220. If a user desires to check a future health state, the state analysis unit may receive, from a user, a time point t at which a user desires to determine his health state, in operation 1230, and may estimate health state information at the further time point t using the bio-signal or the questionary information, in operation 1240.

A parameter extraction unit, such as the parameter extraction unit 120 of FIG. 1, may receive information regarding a user's health state from the state analysis unit to extract avatar parameters using an avatar transformation algorithm, i.e., a relation formula between the predetermined health state information and the avatar parameters, in operation 1250.

An avatar generation unit, such as the avatar generation unit 130 of FIG. 1, may receive parameters defining the avatar from the parameter extraction unit to generate avatar data using the parameters, in operation 1260. A display unit, such as the display unit 140 of FIG. 1, may display an avatar representing the user's health state using the generated avatar data, in operation 1270.

A transmission unit, such as the transmission unit 150 of FIG. 1, may determine whether a user desires to release and transmit the generated avatar data to remote stations or apparatuses, in operation 1280 if a user desires to transmit the avatar data, the transmission unit may receive an address of the remote station or apparatus to which the avatar data will be transmitted, in operation 1290, and then transmit the generated avatar data to the remote station or apparatus, in operation 1295. It may be desirable that the address of the remote station or apparatus be one of a phone number, an e-mail address, and/or an Internet protocol (IP) address, for example.

Embodiments of the present invention may also be embodied as computer readable code on a medium, e.g., a computer-readable recording medium. The medium may be any data storage/transmission device that can store/transmit data which can be thereafter read by a computer system. Examples of the medium may include read-only memory (ROM), random-access memory (RAM), CD-ROMs, magnetic tapes, floppy disks, optical data storage devices, and carrier waves (such as data transmission through the Internet), for example. The medium may also be distributed/stored over network coupled computer systems so that the computer readable code is stored/transferred and implemented in a distributed fashion. Lastly, the computer readable code, e.g., functional programs, codes, code segments, and instructions, to implement embodiments of the present invention can be easily construed by programmers skilled in the art to which the present invention pertains.

As described above, embodiments of the present invention include a method, medium, and apparatus generating an avatar based on the health state of a user. Accordingly, it is possible to provide users with the convenience of recognizing their health state by generating an avatar image describing a user's future health state as well as a user's current health state using bio-signals measured in real-time or questionary information obtained from a user and showing the user the avatar image. Further, it may be possible to induce a user to manage his/her health constantly by maintaining a user's interest due to the avatar image change. Still further, monitoring of health states of family members can be realized by making it possible to transmit the generated avatar image data to remote stations or apparatuses.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus, including at least one processing device, for generating an avatar image using avatar visualization representation parameters, the apparatus comprising:
    a state analyzer to receive information of at least one of a bio-signal and questionary information of a user, analyzes a user's health state based on the received information, and outputs plural health state information of the user based on the analyzed user's health state;
    a parameter extractor using the included at least one processing device to receive the health state information, extract from the received health state information respective avatar visualization representation parameters, defining a change in state or a current state, for representing a health state of each of plural regions of body portions, and implement a formula relating the health state information with the respective avatar visualization representation parameters; and
    an avatar generator to generate the avatar image by changing visual characteristics of at least one body portion of the avatar based on the respective avatar visualization representation parameters,
    wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and
    wherein, in the implementing of the formula relating the health state information with the avatar visualization representation parameters, predetermined first weightings are applied to each of the two or more of the plural state information, as the respective numerical degrees of differently determined health indicators, to determine a first parameter of the avatar visualization representation parameters and predetermined second weightings are applied to each of the two or more of the plural state information to determine a second parameter of the avatar visualization representation parameters.

2. The apparatus of claim 1, wherein the state analyzer receives the at least one of the bio-signal and questionary information of the user and estimates the health state of the user after a predetermined period of time using the health state information, and outputs future health state information for the user.

3. The apparatus of claim 1, wherein the information of bio-signal comprises information of at least one of an electrocardiogram signal, an ultrasonic signal, EDA (electrodermal activity), a body temperature, and a body fat rate.

4. The apparatus of claim 1, wherein the questionary information comprises at least one of information of a habit, a syndrome, a stature, a weight, and a waist measure of the user.

5. The apparatus of claim 1, further comprising a display to displays the generated avatar image.

6. The apparatus of claim 1, further comprising a transmitter to transmit data of the generated avatar image to an remote station or remote apparatus.

7. The apparatus of claim 1, wherein the health state information comprises information of at least one of information defined as identifying whether a hospital visit is required, a stress/fatigue degree, a health age, a skin state, an obesity degree, a body portion balance degree, a heart health degree, a digestive organ health degree, and a respiratory organ health degree.

8. The apparatus of claim 7, wherein the body portion balance degree is representative of being derived using an eight-point tactile electrodes method.

9. The apparatus of claim 1, wherein the parameters comprise at least one of a facial muscle variation rate, a facial skin color variation rate, a facial wrinkle variation rate, a facial width variation rate, a heart size variation rate, a heart color variation rate, a color variation rate of an abnormal portion in a digestive organ, a color variation rate of an abnormal portion in a respiratory organ, and a size variation rate for each body portion depending on a body balance.

10. The apparatus of claim 1, wherein the avatar generator to generate the avatar image using the parameters through at least projecting one of the respective health states onto the generated avatar image by combining a visual indicator, with the generated avatar, to reflect a degree of health for the one respective health state using the visual indicator, wherein the generated avatar includes previously projected health states of the respective health states.

11. The apparatus of claim 1, wherein the avatar generator projects plural independent health states, of the respective health states, onto the generated avatar image, wherein the plural independent health states include plural health states represented in different regions of a face portion of the avatar image and plural health states represented in different regions of a trunk portion of the body portions.

12. The apparatus of claim 1, wherein avatar generator generates the avatar image by graphically changing the visual characteristics of the at least one body portion of the avatar based on the respective parameters to graphically represent a temporal change in the health of the user.

13. The apparatus of claim 1, wherein the respective numerical degrees of differently determined health indicators include a first screening judgment degree (Hs), a stress/fatigue degree (St), a health age (Ha), a skin state (Ag), and an obesity degree (Ob) health state information.

14. The apparatus of claim 1, wherein the parameters are extracted from the health state information according to the equations:

$$A = a1 \times Hs + a2 \times St + a3 \times Ha + a4$$
$$B = b1 \times St + b2 \times Hs + b3 \times Ha + b4$$
$$C = c1 \times St + c2 \times Hs + c3 \times Ha + c4 \times Ag + c5$$
$$D = d1 \times St + d2 \times Hs + d3 \times Ha + d4$$
$$E = e1 \times St + e2 \times Hs + e3 \times Ag + e4$$
$$F = f1 \times Ha + f2 \times Ag + f3$$
$$G = g1 \times Ob + g2$$

where A is a parameter representing the facial muscle variation rate for a first facial region, B is a parameter representing the facial muscle variation rate for a second facial region, C is a parameter representing the facial muscle variation rate for a third facial region, D is a parameter representing the facial muscle variation rate for a fourth facial region, E is a parameter representing the a facial skin color variation rate, F is a parameter representing the facial wrinkle variation rate, and G is a parameter representing the facial width variation rate, and a1, a2, a3, a4, b1, b2, b3, b4, c1, c2, c3, c4, c5, d1, d2, d3, d4, e1, e2, e3, e4, f1, f2, f3, g1 and g2 are constants, and wherein the plural health state information include a first screening judgment degree (Hs), a stress/fatigue degree (St), a health age (Ha), a skin state (Ag), and an obesity degree (Ob) health state information.

15. An apparatus, including at least one processing device, for generating an avatar image using avatar visualization representation parameters, the apparatus comprising:
- a state analyzer using the included at least one processing device to receives at least one of a bio-signal and questionary information of a user, analyzes a user's health state, and outputs plural health state information of the user;
- a parameter extractor using the at least one processing device to receive the health state information, extract avatar visualization representation parameters corresponding to each of plural regions of body portions, and implement a formula relating the health state information with the respective avatar visualization representation parameters; and
- an avatar generator to generate the avatar image by changing visual characteristics of at least one body portion of the avatar based on the respective avatar visualization representation parameters, wherein the state analyzer comprises:
- a bio-signal analyzer to receive at least the one of the bio-signal and questionary information of the user and analyzes the user's health state to output the health state information;
- a storage medium stores the health state information;
- a controller obtains the health state information from the bio-signal analyzer and stores the health state information in the storage medium; and
- a health state estimator to receive the health state information of the user from the bio-signal analyzer and to output a user's future health state information, using a regression formula representing a temporal change in the health state information and health state information of the user stored in the storage medium, and wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and wherein, in the implementing of the formula relating the health state information with the respective avatar visualization representation parameters, predetermined weights are respectively given to each of two or more of the plural health state information, as respective numerical degrees of differently determined health indicators, to respectively derive each of the avatar visualization representation parameters.

16. An apparatus, including at least one processing device, for generating an avatar image using avatar visualization representation parameters, the apparatus comprising:
- a state analyzer to receive information of at least one of a bio-signal and questionary information of a user to analyze a user's health state based on the received information, and outputs plural health state information of the user based on the analyzed user's health state;
- a parameter extractor using the included at least one processing device to receive the health state information, and extract from the received health state information respective avatar visualization representation parameters, defining a change in state or a current state, for representing a health state of each of plural regions of body portions by implementing a formula relating the health state information with the respective avatar visualization representation parameters; and
- an avatar generator to generate the avatar image using the respective avatar visualization representation parameters, wherein the avatar generation unit visually projects onto the avatar image health state information comprising information at least of whether a hospital visit is required, wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and wherein, in the implementing of the formula relating the health state information with the respective avatar visualization representation parameters, predetermined weights are respectively given to each of two or more of the plural health state information, as respective numerical degrees of differently determined health indicators, to respectively derive each of the avatar visualization representation parameters.

17. An apparatus, including at least one processing device, for generating an avatar image using avatar visualization representation parameters, the apparatus comprising:
- a state analyzer to receive information of at least one of a bio-signal and questionary information of a user, analyzes a user's health state based on the received information, and outputs plural health state information of the user based on the analyzed user's health state;

a parameter extractor using the included at least one processing device to receive the health state information, and extract from the received health state information avatar visualization representation parameters by implementing a formula relating the health state information with the respective avatar visualization representation parameters; and an avatar generator to generate the avatar image using the extracted respective avatar visualization representation parameters, wherein the avatar generator uses respective avatar visualization representation parameters of the extracted avatar visualization representation parameters to visually project onto the avatar image at least one of a facial muscle variation rate, a facial skin color variation rate, a facial wrinkle variation rate, a facial width variation rate, a heart size variation rate, a heart color variation rate, a color variation rate of an abnormal portion in a digestive organ, a color variation rate of an abnormal portion in a respiratory organ, and a size variation rate for each body portion depending on a body balance, and wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and wherein, in the implementing of the formula relating the health state information with the respective avatar visualization representation parameters, predetermined weights are respectively given to each of two or more of the plural health state information, as respective numerical degrees of differently determined health indicators, to respectively derive each of the avatar visualization representation parameters.

18. A method for generating an avatar image using avatar visualization representation parameters, comprising:

analyzing a user's health state using information of at least one of a bio-signal and questionary information of the user and outputting plural health state information of the user based on the analyzed user's health state;

receiving the health state information and obtaining a formula relating the health state information of the user with parameters;

extracting the avatar visualization representation parameters, from the received health state information, as respective avatar visualization representation parameters, defining a change in state or a current state, for representing respective health states of each of plural defined regions within each of plural different body portions based on the formula; and generating, using at least one processing device, the avatar image by changing visual characteristics of at least one of the body portions of the avatar based on the extracted respective avatar visualization representation parameters, wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and wherein, in implementing the formula relating the health state information with the respective avatar visualization representation parameters, predetermined weights are respectively given to each of two or more of the plural health state information, as respective numerical degrees of differently determined health indicators, to respectively derive each of the avatar visualization representation parameters.

19. The method of claim 18, wherein the analyzing comprises estimating the user's health state for after a predetermined period of time using the at least one of the user's bio-signal and the questionary information.

20. The method of claim 18, wherein the information of the bio-signal comprises information of at least one of an electrocardiogram signal, an ultrasonic signal, EDA(electrodermal activity), a body temperature, and a body fat rate.

21. The method of claim 18, wherein the questionary information comprises at least one of information regarding a habit, a syndrome, a stature, a weight, and a waist measure.

22. The method of claim 18, further comprising displaying data of the generated avatar image.

23. The method of claim 18, further comprising transmitting data of the generated avatar image to a remote station or apparatus.

24. The method of claim 18, wherein the health state information comprises information of at least one of information defined as identifying whether a hospital visit is required, a stress/fatigue degree, a health age, a skin state, an obesity degree, a body portion balance degree, a heart health degree, a digestive organ health degree, and a respiratory organ health degree.

25. The method of claim 24, wherein the body portion balance degree is representative of being derived using an eight-point tactile electrodes method.

26. The method of claim 18, wherein the parameters comprise at least one of a facial muscle variation rate, a facial skin color variation rate, a facial wrinkle variation rate, a facial width variation rate, a heart size variation rate, a heart color variation rate, a color variation rate of an abnormal portion in a digestive organ, a color variation rate of an abnormal portion in a respiratory organ, and a size variation rate for each body portion depending on a body balance.

27. The method of claim 18, wherein the generating of the avatar image generates the avatar image using the parameters through at least projecting one of the respective health states onto the generated avatar image by combining a visual indicator, with the generated avatar, to reflect a degree of health for the one respective health state using the visual indicator, wherein the generated avatar includes previously projected health states of the respective health states.

28. The method of claim 18, wherein the generating of the avatar image includes projecting plural independent health states, of the respective health states, onto the generated avatar image, wherein the plural independent health states include plural health states represented in different regions of a face portion of the avatar image and plural health states represented in different regions of a trunk portion of the body portions.

29. The method of claim 18, wherein the generating of the avatar image by the graphically changing of the visual characteristics of the at least one body portion of the avatar is based on the respective parameters to graphically represent a temporal change in the health of the user.

30. The method of claim 18, wherein, in the implementing of the formula relating the health state information with the parameters, predetermined first weightings are applied to each of the two or more of the plural state information, as the respective numerical degrees of differently determined health indicators, to determine a first parameter of the parameters and predetermined second weightings are applied to each of the two or more of the plural state information to determine a second parameter of the parameters.

31. The method of claim 18, wherein the respective numerical degrees of differently determined health indicators include a first screening judgment degree (Hs), a stress/fatigue degree (St), a health age (Ha), a skin state (Ag), and an obesity degree (Ob) health state information.

32. A method for generating an avatar image using avatar visualization representation parameters, comprising:
   analyzing a user's health state using at least one of a bio-signal and questionary information of the user;
   receiving information of the analyzed health state and obtaining a formula relating plural health state information of the user with parameters;
   extracting the avatar visualization representation parameters corresponding to each of plural regions of body portions ; and
   generating, using at least one processing device, the avatar image by changing visual characteristics of at least one body portion of the avatar based on the extracted respective avatar visualization representation parameters, wherein the analyzing comprises:
   analyzing the user's health state using the at least one of the bio-signal and the questionary information of the user;
   obtaining a regression formula representing a temporal change in the health state information from the analyzed user's health state; and
   generating future health state information of the user of after a predetermined period of time, using the health state information and the regression formula,
   wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and
   wherein, in implementing the formula relating the health state information with the respective avatar visualization representation parameters, predetermined weights are respectively given to each of two or more of the plural health state information, as respective numerical degrees of differently determined health indicators, to respectively derive each of the avatar visualization representation parameters.

33. A method for generating an avatar image using avatar visualization representation parameters, comprising:
   analyzing a user's health state using information of at least one of a bio-signal and questionary information of the user and outputting plural health state information of the user based on the analyzed user's health state;
   receiving the health state information and obtaining a formula relating the health state information of the user with parameters;
   extracting the avatar visualization representation parameters from the received health state information, as respective avatar visualization representation parameters, defining a change in state or a current state, for representing a health state of each of plural regions of body portions; and
   generating, using at least one processing device, the avatar image using the respective avatar visualization representation parameters,
   wherein the generating of the avatar image further comprises projecting onto the avatar information defined as identifying whether a hospital visit is required, and
   wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and
   wherein, in implementing the formula relating the health state information with the respective avatar visualization representation parameters, predetermined weights are respectively given to each of two or more of the plural health state information, as respective numerical degrees of differently determined health indicators, to respectively derive each of the avatar visualization representation parameters.

34. A method for generating an avatar image using avatar visualization representation parameters, comprising:
   analyzing a user's health state using information of at least one of a bio-signal and questionary information of the user and outputting plural health state information of the user based on the analyzed user's health state;
   receiving the health state information and obtaining a formula relating health state information of the user with parameters;
   extracting the avatar visualization representation parameters, as avatar visualization representation parameters, from the received health state information; and
   generating, using at least one processing device, the avatar image using the extracted avatar visualization representation parameters,
   wherein the parameters comprise at least one from among a facial muscle variation rate, a facial skin color variation rate, a facial wrinkle variation rate, a facial width variation rate, a heart size variation rate, a heart color variation rate, a color variation rate of an abnormal portion in a digestive organ, a color variation rate of an abnormal portion in a respiratory organ, and a size variation rate for each body portion depending on a body balance, and
   wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and
   wherein, in the implementing of the formula relating the health state information with the respective avatar visualization representation parameters, predetermined weights are respectively given to each of two or more of the plural health state information, as respective numerical degrees of differently determined health indicators, to respectively derive each of the avatar visualization representation parameters.

35. The method of claim 34, wherein, in the generating of the avatar image, the avatar image is generated by graphically changing the visual characteristics of the at least one body portion of the avatar based on the respective parameters to graphically represent a temporal change in the health of the user.

36. A non-transitory computer readable recording medium comprising computer readable code to implement the method of claim 34.

37. An apparatus, including at least one processing device, for generating an avatar image using avatar visualization representation parameters, the apparatus comprising:
 a state analyzer to receive information of at least one of a bio-signal and questionary information of a user to analyze a user's health state based on the received information, and outputs health state information of the user based on the analyzed user's health state;
 a parameter extractor using the included at least one processing device to receive the health state information, and extracts from the received health state information avatar visualization representation parameters, defining a change in state or a current state, for representing a health state of each of plural regions of body portions in the avatar image by implementing a formula relating the health state information with the avatar visualization representation parameters; and
 an avatar generator to generate the avatar image using the extracted avatar visualization representation parameters and projects a corresponding health state onto the generated avatar image by combining a visual indicator, with the generated avatar, to reflect a degree of the corresponding health state,
 wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and
 wherein, in the implementing of the formula relating the health state information with the respective avatar visualization representation parameters, predetermined weights are respectively given to each of two or more of the plural health state information, as respective numerical degrees of differently determined health indicators, to respectively derive each of the avatar visualization representation parameters.

38. The apparatus of claim 37, wherein the state analyzer to receive the at least one of the bio-signal and questionary information of the user, estimates the health state of the user after a predetermined period of time using the health state information, and outputs future health state information for the user.

39. The apparatus of claim 37, wherein the information of the bio-signal comprises information of at least one of an electrocardiogram signal, an ultrasonic signal, EDA (electrodermal activity), a body temperature, and a body fat rate.

40. The apparatus of claim 37, wherein the questionary information comprises at least one of information of a habit, a syndrome, a stature, a weight, and a waist measure of the user.

41. The apparatus of claim 37, wherein the health state information comprises information of at least one of information defined as identifying whether a hospital visit is required, a stress/fatigue degree, a health age, a skin state, an obesity degree, a body portion balance degree, a heart health degree, a digestive organ health degree, and a respiratory organ health degree.

42. The apparatus of claim 37, wherein the body portion balance degree is representative of being derived using an eight-point tactile electrodes method.

43. The apparatus of claim 37, further comprising a display to display the generated avatar image.

44. The apparatus of claim 37, further comprising a transmitter to transmit data of the generated avatar image to an remote station or remote apparatus.

45. The apparatus of claim 37, where the visual indicator combined with the generated avatar is controlled to reflect a degree of the corresponding health state through different colors.

46. An apparatus, including at least one processing device, for generating an avatar image using avatar visualization representation parameters, the apparatus comprising:
 a state analyzer to receive at least one of a bio-signal and questionary information of a user to analyze a user's health state, and outputs health state information of the user;
 a parameter extractor using the included at least one processing device to receives the health state information, and extracts avatar visualization representation parameters, defining a change in state or a current state, for representing a health state of each of plural regions of body portions in the avatar image by implementing a formula relating the health state information with the respective avatar visualization representation parameters; and
 an avatar generator to generate the avatar image using the respective avatar visualization representation parameters and projects a corresponding health state onto the generated avatar image by combining a visual indicator with the generated avatar to reflect a degree of the corresponding health state, wherein the state analyzer comprises:
 a bio-signal analysis unit analyzer to receive at least the one of the bio-signal and questionary information of the user, analyzes the user's health state, and output the health state information;
 a storage medium stores the health state information;
 a controller obtains the health state information from the bio-signal analyzer stored in the storage medium; and
 a health state estimator to receive the health state information of the user from the bio-signal analyzer and to output a user's future health state information, using a regression formula representing a temporal change in the health state information and health state information of the user stored in the storage medium,
 wherein the avatar generator is configured to project based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and
 wherein, in the implementing of the formula relating the health state information with the respective avatar visualization representation parameters, predetermined weights are respectively given to each of two or more of the plural health state information, as respective numerical degrees of differently determined health indicators, to respectively derive each of the avatar visualization representation parameters.

47. A method for generating an avatar image using avatar visualization representation parameters, comprising:
analyzing a user's health state using information of at least one of a bio-signal and questionary information of the user and outputting health state information of the user based on the analyzed user's health state;
receiving the health state information and obtaining a formula relating the health state information of the user with the respective avatar visualization representation parameters;
extracting the respective avatar visualization representation parameters, as avatar visualization representation parameters, from the received health state information; and
generating, using at least one processing device, the avatar image using the extracted avatar visualization representation parameters through at least projecting a corresponding health state onto the generated avatar image by combining a visual indicator, with the generated avatar to reflect a degree of the corresponding health state,
wherein the generating of the avatar image includes projecting based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and
wherein, in the implementing of the formula relating the health state information with the respective avatar visualization representation parameters, predetermined weights are respectively given to consideration of each of two or more of the plural health state information, as respective numerical degrees of differently determined health indicators, to respectively derive each of the avatar visualization representation parameters.

48. The method of claim 47, wherein the analyzing comprises estimating the user's health state for after a predetermined period of time using the at least one of the user's bio-signal and the questionary information.

49. The method of claim 47, wherein the information of the bio-signal comprises information of at least one of an electrocardiogram signal, an ultrasonic signal, EDA (electrodermal activity), a body temperature, and a body fat rate.

50. The method of claim 47, wherein the questionary information comprises at least one of information regarding a habit, a syndrome, a stature, a weight, and a waist measure.

51. The method of claim 47, wherein the generating of the avatar image further comprises projecting onto the avatar image health state information comprising information of at least one of information defined as indicating whether a hospital visit is required, a stress/fatigue degree, a health age, a skin state, a body portion balance degree, a heart health degree, a digestive organ health degree, and a respiratory organ health degree.

52. The method of claim 51, wherein the body portion balance degree is representative of being derived using an eight-point tactile electrodes method.

53. The method of claim 47, wherein the parameters comprise at least one of a facial muscle variation rate, a facial skin color variation rate, a facial wrinkle variation rate, a facial width variation rate, a heart size variation rate, a heart color variation rate, a color variation rate of an abnormal portion in a digestive organ, a color variation rate of an abnormal portion in a respiratory organ, and a size variation rate for each body portion depending on a body balance.

54. The method of claim 47, further comprising displaying data of the generated avatar image.

55. The method of claim 47, further comprising transmitting data of the generated avatar image to a remote station or apparatus.

56. The method of claim 47, where the visual indicator combined with the generated avatar reflects a degree of the corresponding health state through different colors.

57. A method for generating an avatar image using avatar visualization representation parameters, comprising:
analyzing a user's health state using at least one of a bio-signal and questionary information of the user;
receiving information of the analyzed health state and obtaining a formula relating health state information of the user with avatar visualization representation parameters;
extracting the avatar visualization representation parameters; and
generating, using at least one processing device, the avatar image using the extracted avatar visualization representation parameters through at least projecting a corresponding health state onto the generated avatar image by combining a visual indicator with the generated avatar to reflect a degree of the corresponding health state, wherein the analyzing comprises:
analyzing the user's health state using the at least one of the bio-signal and the questionary information of the user;
obtaining a regression formula representing a temporal change in the health state information from the analyzed user's health state; and
generating future health state information of the user of after a predetermined period of time, using the health state information and the regression formula,
wherein the generating of the avatar image includes projecting based on the respective avatar visualization representation parameters, a respective health state for one or more particular body portions, of the respective health states, onto the generated avatar image by manipulating one or more regions of another portion of the avatar image that is independent of the particular one or more body portions for which the respective health states are projected, and
wherein, in the implementing of the formula relating the health state information with the respective avatar visualization representation parameters, predetermined weights are respectively given to each of two or more of the plural health state information, as respective numerical degrees of differently determined health indicators, to respectively derive each of a the avatar visualization representation parameters.

58. A non-transitory computer readable recording medium comprising computer readable code to implement the method of claim 51.

* * * * *